(12) United States Patent
Horton et al.

(10) Patent No.: US 10,420,602 B2
(45) Date of Patent: Sep. 24, 2019

(54) TREATMENT DEVICE USING R.F. ELECTRICAL CURRENT FOR HEATING A FIRST INNER REGION AND A SECOND INNER REGION OF SKIN

(71) Applicant: KONINKLIJKE PHILIPS N.V., Eindhoven (NL)

(72) Inventors: Margaret Ruth Horton, Eindhoven (NL); Jonathan Alambra Palero, Eindhoven (NL); Martin Jurna, Eindhoven (NL); Babu Varghese, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 349 days.

(21) Appl. No.: 15/324,500

(22) PCT Filed: Jun. 8, 2015

(86) PCT No.: PCT/EP2015/062642
§ 371 (c)(1),
(2) Date: Jan. 6, 2017

(87) PCT Pub. No.: WO2016/012147
PCT Pub. Date: Jan. 28, 2016

(65) Prior Publication Data
US 2017/0202606 A1     Jul. 20, 2017

(30) Foreign Application Priority Data
Jul. 24, 2014   (EP) ..................................... 14178253

(51) Int. Cl.
*A61B 18/14* (2006.01)
*A61B 18/12* (2006.01)
(Continued)

(52) U.S. Cl.
CPC .......... *A61B 18/14* (2013.01); *A61B 18/1206* (2013.01); *A61N 1/28* (2013.01);
(Continued)

(58) Field of Classification Search
CPC ................ A61B 18/1206; A61B 18/14; A61B 2018/0016; A61B 2018/0047;
(Continued)

(56) References Cited

U.S. PATENT DOCUMENTS 6,413,255 B1 *   7/2002  Stern ...................... A61B 18/14
                                                              606/41
8,359,104 B2    1/2013  Epstein
(Continued)

FOREIGN PATENT DOCUMENTS

KR        101065611 B1     9/2011
WO        2012052986 A2    4/2012

OTHER PUBLICATIONS

"Radio Frequency Energy for Non-invasive and Minimally Invasive Skin Tightening", by R.Stephen Mulholland, Clin Plastic Surg 38 (2011) 437-448.

*Primary Examiner* — Michael F Peffley

(57) ABSTRACT

The invention provides a non-invasive treatment device (100) for heating a first (15) and a second (25) inner region of skin using r.f. electrical current, comprising: a first r.f. treatment electrode (10) configured and arranged to allow r.f. current to pass through the first inner region (15) to a return electrode (340), a second r.f. treatment electrode (20) configured and arranged to allow r.f. current to pass through the second inner region (25) to the return electrode (340), the device further being arranged such that the smallest distance between the first r.f. treatment electrode (10) and the return electrode (340) is less than the smallest distance between the second r.f. treatment electrode (20) and the return electrode
(Continued)

(340); wherein the electrical skin contact area of the return electrode (340) is 5 or more times larger than the electrical skin contact area of the first r.f. treatment electrode (10), and the electrical skin contact area of the second r.f. treatment electrode (20) is 5 or more times larger than the electrical skin contact area of the first r.f. treatment electrode (10). By incorporating the second and first treatment electrodes in the same device, or probe, the positional relationship between the first and second regions being heated is fixed, or at least more predictable. By means of a suitable configuration, the regions may coincide to a smaller or greater degree. In some cases, the configuration may allow the same skin condition to be treated using heating of the first and second inner regions without moving the device over the skin. By providing an electrical skin contact area of the return electrode which is 5 or more times larger than the electrical skin contact area of the first r.f. treatment electrode, the locations heated by the r.f. electrical current will be proximate to the first treatment electrode, reducing the possibility of undesirable hotspots proximate the return electrode (340).

4 Claims, 4 Drawing Sheets

(51) Int. Cl.
| | | |
|---|---|---|
| *A61N 1/28* | (2006.01) | |
| *A61N 1/32* | (2006.01) | |
| *A61B 18/00* | (2006.01) | |

(52) U.S. Cl.
CPC ...... *A61N 1/328* (2013.01); *A61B 2018/0016* (2013.01); *A61B 2018/0047* (2013.01); *A61B 2018/1273* (2013.01); *A61B 2018/1467* (2013.01)

(58) Field of Classification Search
CPC .... A61B 2018/1273; A61B 2018/1467; A61N 1/28; A61N 1/328
See application file for complete search history.

(56) References Cited

U.S. PATENT DOCUMENTS

| | | | |
|---|---|---|---|
| 8,496,654 | B2 | 7/2013 | Adanny |
| 8,512,331 | B2* | 8/2013 | Lischinsky ........ A61B 18/1206 |
| | | | 606/34 |
| 8,700,176 | B2 | 4/2014 | Azar |
| 9,108,036 | B2* | 8/2015 | Adanny ............. A61B 18/1233 |
| 9,827,437 | B2* | 11/2017 | Lischinsky ........ A61N 1/36014 |
| 2008/0183251 | A1 | 7/2008 | Azar |
| 2011/0015625 | A1 | 1/2011 | Adanny |
| 2012/0023129 | A1 | 1/2012 | Vedula |
| 2012/0310232 | A1 | 12/2012 | Erez |
| 2013/0138100 | A1 | 5/2013 | Bystryak |
| 2013/0282085 | A1 | 10/2013 | Lischinsky |
| 2013/0289679 | A1* | 10/2013 | Eckhouse ............. A61N 1/403 |
| | | | 607/102 |
| 2014/0005658 | A1* | 1/2014 | Rosenbegr ............ A61B 18/18 |
| | | | 606/33 |

* cited by examiner

TREATMENT DEVICE USING R.F. ELECTRICAL CURRENT FOR HEATING A FIRST INNER REGION AND A SECOND INNER REGION OF SKIN

This application is the U.S. National Phase application under 35 U.S.C. § 371 of International Application No. PCT/EP2015/062642, filed on Jun. 8, 2015, which claims the benefit of International Application No. 14178253.2 filed on Jul. 24, 2014. These applications are hereby incorporated by reference herein.

FIELD OF THE INVENTION

The invention relates generally to a treatment device for skin, in particular to a non-invasive treatment device for skin treatment by using a radio-frequency (r.f.) electrical current.

BACKGROUND OF THE INVENTION

Various forms of electromagnetic radiation, particularly laser light beams, have been used for many years for a variety of therapeutic and non-therapeutic treatments of the skin, such as hair removal, skin rejuvenation to reduce wrinkles, and the treatment of conditions like acne, actinic keratoses, blemishes, scar tissue, discoloration, vascular lesions, cellulite and tattoo removal. Most of these treatments rely on photothermolysis, wherein a treatment location in the skin is targeted by the treatment radiation. For example, to treat wrinkles, the dermis layer of the skin is damaged by heating (thermolysis) to induce a wound response, while minimizing damage to the epidermis layer of the skin.

Radio-frequency (usually abbreviated as r.f. or rf) energy has also been used for skin rejuvenation and skin tightening in both the professional and home-use aesthetic treatment devices market. Home-use devices are frequently used for non-therapeutic or cosmetic treatments. Compared to laser treatment devices, r.f. treatment devices have a substantially lower cost price and can provide larger volume deep tissue contraction. Additionally, r.f. energy dissipation does not rely on the absorption of light by chromophores, so that tissue pigmentation does not interfere with the delivery of energy. The advantages of r.f. treatments over laser treatments, and some embodiments of known r.f. treatment devices, are described in the article "Radio Frequency Energy for Non-invasive and Minimally Invasive Skin Tightening", by R. Stephen Mulholland, Clin Plastic Surg 38 (2011) 437-448.

The basic principle of r.f. energy delivery at the skin surface to skin tissue is that an alternating current is applied in a closed circuit with the skin. The r.f. energy is dissipated as thermal energy primarily due to intramolecular vibrations. The thermal effects range from sub-epidermal tissue contraction to skin surface damages, e.g. cell necrosis and ablation. These effects have different desired effects on the skin. Skin surface damages are used for skin rejuvenation of the epidermis or to enhance the penetration of substances, while sub-epidermal tissue contraction is primarily used for skin tightening purposes and to stimulate new collagen synthesis.

The thermal effects generated depend on the properties of the r.f. energy delivered (frequency, power, duration), the treatment regime and the electrode configuration (size, inter-electrode distance, use of conductive substance). An r.f. treatment of a certain condition may require more than one treatment to be performed at the same or proximal locations to generate the same, similar or different thermal effects. Traditional devices inevitably require a range of r.f. treatment heads or probes to perform each separate treatment, because the dimensions and configurations of the r.f. electrodes used in each probe are fixed, and each probe can only provide a limited range of treatments. This increases the costs of the r.f. treatment device, and may require the use of more than one probe during a single treatment session. This complicates any treatment regime, and increases the risk of operating errors, and may lead in some cases to an ineffective treatment. In extreme cases, confusion about treatment settings and the appropriate probe to be applied may also result in unnecessary pain felt by the person being treated, or unnecessary skin damage such as burning or charring.

US 2013/0289679 A1 discloses an apparatus for personal aesthetic skin treatment comprising a carrier with a plurality of miniature voltage-to-skin applying electrodes surrounded by a common return electrode. With this apparatus, an asymmetric distribution of impedances is provided along the different paths of current between the voltage-to-skin applying electrodes and the common return electrode. In particular a high impedance exists below the voltage-to-skin applying electrodes, while a low impedance exists in the return path to the return electrodes. As a result, heating of the skin tissue is focussed to small volumes of the skin below the voltage-to-skin electrodes, resulting in fractional treatment of the skin tissue.

U.S. Pat. No. 8,700,176 B2 discloses a skin treating device for delivering RF energy to the skin, including one or more RF generating units, multiple RF electrode groups, and a controller for controllably applying RF energy to the skin through any selected RF electrode group or any selected RF electrode group combination. The RF electrodes may be stationary and/or movable. Different RF frequencies may be used. With this device, the alternation of energy application through different electrode groups at different times, and/or the changing of the inter-electrode distance and configuration by using moving RF electrodes may reduce or prevent electrode overheating, control RF energy distribution within the skin, and enable use of the device for different skin treatment applications.

US 2012/0310232 A1 discloses a system for treating skin tissue using multiple energy types. The system may include at least two transducers configured to produce sound waves at the surface and in the inner layers of the skin. In addition a plurality of RF electrodes may be configured to emit a plurality of RF signals. In an embodiment a selected RF electrode and a first subset of RF electrodes are used to induce a first electro-magnetic field in a first layer of the skin. Subsequently or simultaneously, the selected RF electrode and a second subset of RF electrodes is used to induce a second electro-magnetic field in a second layer of the skin.

US 2013/0282085 A1 discloses a skin treatment device for home use by means of which RF energy is delivered to a relatively small and well localized volume of the skin, avoiding excessive heating of the skin surface. With this device, skin surface heating is monitored both by temperature measurement and by movement monitoring of the device to ensure proper use and prevent skin overheating and the pain associated therewith. The device comprises a linear array of RF electrodes, and a control unit configured to designate reversed polarities to subgroups of the electrodes and to control the phase of each electrode. In particular the control unit may be arranged to set any specified phase between any two electrodes to exactly control energy delivery to the skin.

SUMMARY OF THE INVENTION

An object of the invention is to improve a non-invasive treatment device using a radio-frequency electrical current. In particular, an object of the invention is to provide an r.f. skin treatment device that is both non-invasive and provides effective and reproducible results for multiple treatments.

The object is achieved according to the invention by a non-invasive treatment device for heating a first inner region and a second inner region of skin using radio-frequency (r.f.) electrical current, the second inner region being at a deeper location in the skin than the first inner region, the device comprising:

a first r.f. treatment electrode configured and arranged to allow r.f. electrical current to pass through an outer surface of the skin and through the first inner region;

a return electrode configured and arranged to allow r.f. electrical current to pass through the first inner region and the outer surface of the skin;

a first r.f. generator configured and arranged such that, in use for heating the first inner region, a first r.f. current is applied through the first inner region between the first r.f. treatment electrode and the return electrode operating in bipolar mode;

a second r.f. treatment electrode configured and arranged to allow r.f. electrical current to pass through the outer surface of the skin and through the second inner region;

the return electrode being further configured and arranged to allow r.f. electrical current to pass through the second inner region and the outer surface of the skin; and a second r.f. generator configured and arranged such that, in use for heating the second inner region, a second r.f. current is applied through the second inner region between the second r.f. treatment electrode and the return electrode operating in bipolar mode;

the device further being arranged such that a smallest distance between the first r.f. treatment electrode and the return electrode is less than a smallest distance between the second r.f. treatment electrode and the return electrode;

wherein the first r.f. treatment electrode, the second r.f. treatment electrode and the return electrode each comprise an electrical skin contact area, the electrical skin contact area of the return electrode being 5 or more times larger than the electrical skin contact area of the first r.f. treatment electrode, the treatment device being characterized in that the electrical skin contact area of the second r.f. treatment electrode is 5 or more times larger than the electrical skin contact area of the first r.f. treatment electrode, and in that the device further comprises a controller to selectively activate the first r.f generator and the second r.f. generator either simultaneously or alternately.

R.f. energy is typically applied in two main areas of interest, i.e. skin rejuvenation and skin tightening. Currently, each of these areas of interest requires a separate device for full efficacy, or at least two or more different probes or hand-pieces.

Skin rejuvenation is generally achieved by intentionally heating an inner (or first) region of skin, proximate to the skin surface and the r.f. treatment electrode, to a temperature that is significantly above normal body temperature, typically to a temperature above 55 degrees C., so as to induce collagen denaturation and/or coagulation and/or full ablation of the epidermal skin tissue. This heating causes collagen and epidermal tissue re-modelling, resulting in a rejuvenated skin. To minimize downtime and side effects while maintaining sufficiently high efficacy levels, skin rejuvenation is often performed on a fractional area of the skin surface through the creation of distributed small lesions in first inner regions of the skin close to the skin surface, typically 100-300 microns in size and usually by achieving a temperature in a range between 65-90 degrees C. An r.f. treatment device to generate a fractional pattern of such first inner regions of the skin is disclosed in PCT application WO 2012/023129.

Skin tightening is a non-ablative treatment based on thermolysis by heating an inner (or second) region of the skin, in particular in the dermal skin layer, wherein the second inner region is at a substantially deeper location in the skin and in most cases greater in volume than the first inner region which is the targeted treatment region for skin rejuvenation. Typically, the target of the second inner region is the dermis layer, which is at least 0.5 mm below the outer surface of the skin.

Particularly for skin tightening, the heating occurs further away from the r.f. treatment electrode, i.e. at a deeper location in the skin, and over a larger volume as compared with skin rejuvenation. Dermal collagen denatures and contracts or shrinks when heated at temperatures above 55 degrees C. In general, a 5 degree rise of the treatment temperature results in a tenfold reduction of the treatment time. For example, a treatment temperature of 65 degrees C. requires a treatment time of approximately 200 s, and a treatment temperature of 70 degrees C. requires a treatment time of approximately 20 s. The shrinkage of the collagen tissue can reach tens of percents of the heated tissue volume, and results in tightening of the skin and reduction of wrinkles, fine lines and skin sagging. Furthermore, this thermal treatment also rejuvenates the skin by stimulating the synthesis of new collagen. R.f. treatment devices are widely used in conventional techniques for skin tightening, as disclosed in the Mulholland article mentioned above, in which such second inner regions of the skin are heated, which are at a deeper location in the skin and have a larger volume than the first inner regions heated during rejuvenation treatments.

The first inner region of the skin is located between the first r.f. treatment electrode and the return electrode. During use, to promote skin rejuvenation, the first electrode and the return electrode operate in bipolar mode.

The second inner region of the skin is located between the second r.f. treatment electrode and the return electrode. During use, to promote skin tightening, the second electrode and the return electrode operate in bipolar mode.

Both the first inner region and the second inner region extend from an outer surface of the skin into an inner region of skin. The second inner region extends deeper into the skin than the first inner region, because the tightening effect is promoted by heating the dermal collagen tissue such that it denatures and shrinks. During operation, the first inner region is located more proximate to the surface of the skin and the electrodes of the treatment device than the second inner region, and the rejuvenation effect is promoted by inducing collagen denaturation and/or coagulation and/or full ablation of skin tissue in the upper layer of the skin, such as the epidermis or upper dermis.

The volume of the first inner region is determined, inter alia, by the electrical skin contact areas of the first r.f. treatment electrode and the return electrode. The volume of the second inner region is determined, inter alia, by the electrical skin contact areas of the second r.f. treatment electrode and the return electrode.

In general, the volume of the second inner region is significantly larger than the volume of the first inner region. The ratio of the volumes of the second inner region and the first inner region is determined, inter alia, by the ratio of the electrical skin contact areas of the second pair of electrodes compared to the first pair of electrodes.

The invention is based on the insight that it may be advantageous to provide an r.f. skin treatment device capable of providing a broader range of skin treatments at multiple tissue depths and areas, wherein the proximity of the first inner region and the second inner region of the skin may be more accurately controlled. The main reason for using different probes is that an electrode configuration for skin rejuvenation (e.g. the e-Matrix of Syneron-Candela) is not suitable for skin tightening applications, primarily due to its very small treatment electrode size. Even the use of arrays of multiple treatment electrodes does not improve the suitability for skin tightening, because each treatment electrode heats a separate first inner region of the skin only.

By adding the functionality of a tightening electrode to the treatment device, both skin rejuvenation and skin tightening treatments become possible with the same probe or hand-piece. These treatments may be performed alternately or simultaneously, and repeated in any sequence. According to the invention, the return electrode is used both in combination with the first r.f. treatment electrode for skin rejuvenation and in combination with the second r.f. treatment electrode for skin tightening, so that a relatively simple configuration of the electrodes is achieved.

An additional advantage is achieved when the skin rejuvenation treatment and the skin tightening treatment are performed without changing the position of the probe on the skin. The predetermined spatial relationship between the first inner region and the second inner region of the skin may decrease the healing time under certain conditions. For example, WO 2014/045216 describes how the healing time of a dermal lesion is accelerated by applying an epidermal heat stimulus in a region proximate to or coinciding with the region of dermal lesions. Performing such a treatment regime by using more than one probe would normally require marking the skin to indicate where the probes should be placed relative to each other, or using some other kind of reference.

A further advantage of the invention is the synergistic improvement in skin appearance by applying both skin rejuvenation and skin tightening treatments at the same location. Especially when the appearance of fine lines and wrinkles is to be treated, both skin rejuvenation and skin tightening are known to have a positive effect. The invention provides a device that is able to provide both treatments at the same position on the skin. The device may also be arranged to have a relatively small skin contact surface area, allowing facial lines to be treated conveniently.

By providing the return electrode with an electrical skin contact area which is 5 or more times larger than the electrical skin contact area of the first r.f. treatment electrode, the skin regions effectively heated by the r.f. electrical current will be proximate to the first r.f. treatment electrode, thereby reducing the possibility of undesirable hotspots proximate to the return electrode.

In an embodiment of the treatment device according to the invention, when the treatment device is in operation for heating the first inner region, the second r.f. treatment electrode is configured and arranged as a further return electrode to allow r.f. electrical current to pass through the first inner region and the outer surface of skin, and wherein the first r.f. generator is configured and arranged such that an r.f. electrical current is applied between the first r.f. treatment electrode and both the return electrode and the further return electrode through the first inner region, and wherein a total of the electrical skin contact areas of the return electrode and the further return electrode is 5 or more times larger than the electrical skin contact area of the first r.f. treatment electrode.

The additional use of the further return electrode increases the total of the electrical skin contact areas of the return electrodes. Such an increased electrical skin contact area even more reduces the risk of undesired heating below the return electrodes during the heating of the first inner region of the skin, so that the heat generated is concentrated to a higher degree below the smaller first r.f. treatment electrode. By utilizing the further return electrode, the ratio between the electrical skin contact areas of the return electrodes and the first r.f. treatment electrode may exceed 5 or more within a smaller device.

In an embodiment of the treatment device according to the invention, a maximum dimension of the first r.f. treatment electrode proximate the electrical skin contact area of the first r.f. treatment electrode is less than or equal to 1 mm. This maximum dimension is measured in a cross-section of the electrical skin contact area which is proximate and approximately parallel to the outer surface of the skin during use. This maximum dimension is advantageous, because the heating of the first inner region of the skin will take place more proximate to the first r.f. treatment electrode.

In an embodiment of the treatment device according to the invention, the device comprises a plurality of first r.f. treatment electrodes, the plurality of first r.f. treatment electrodes and the return electrode being configured and arranged to allow r.f. electrical current to pass through the outer surface of the skin and through a plurality of first inner regions, and the first r.f. generator is configured and arranged to apply the r.f. electrical current to each of the plurality of first r.f. treatment electrodes and to each of the plurality of first inner regions of the skin either alternately or simultaneously.

In this embodiment, more than one first inner region of the skin can be treated with an appropriate r.f. electrical current. In a simple embodiment, each of the plurality of first r.f. treatment electrodes is provided with the same r.f. electrical current at the same time. However, the first r.f. treatment electrodes may also be provided with mutually different r.f. electrical currents at mutually different times, or the first r.f. treatment electrodes may be groupwise provided with similar r.f. energies. This allows a larger area to be treated for skin rejuvenation, with the device in a single position on the skin, and better control of the energy distribution within the inner skin region at multiple depths.

In an embodiment of the treatment device according to the invention, which provides a maximum degree of flexibility in treatments in a similar manner, the device comprises a plurality of second r.f. treatment electrodes, the plurality of second r.f. treatment electrodes and the return electrode being configured and arranged to allow r.f. electrical current to pass through the outer surface of the skin and through a plurality of second inner regions of the skin, and the second r.f. generator is configured and arranged to apply r.f. electrical current to each of the plurality of second r.f. treatment electrodes and to each of the plurality of second inner regions of the skin either alternately or simultaneously.

In this embodiment, more than one second inner region of the skin can be treated with an appropriate r.f. electrical current. In a simple embodiment, each of the plurality of second r.f. treatment electrodes is provided with the same r.f.

electrical current during the treatment time. However, the second r.f. treatment electrodes may also be provided with mutually different r.f. electrical currents during mutually different times, or the second r.f. treatment electrodes may be groupwise provided with similar r.f. energies. This allows a larger area to be treated for skin tightening, with the device in a single position on the skin, and better control of the energy distribution within the inner skin region at multiple depths.

The treatment device according to the invention may be advantageously used in the treatment of skin conditions, in particular wrinkles, fine lines, laxity, sagging skin, acne, actinic keratoses, blemishes, scar tissue or discoloration. Many of these conditions are treated in non-therapeutic or cosmetic treatments.

It should be noted that items which have the same reference numbers in different Figures have the same structural features and the same functions, or represent similar signals. Where the function and/or structure of such an item has been explained, there is no necessity for repeated explanation thereof in the detailed description.

DETAILED DESCRIPTION OF EMBODIMENTS

Figure 1:
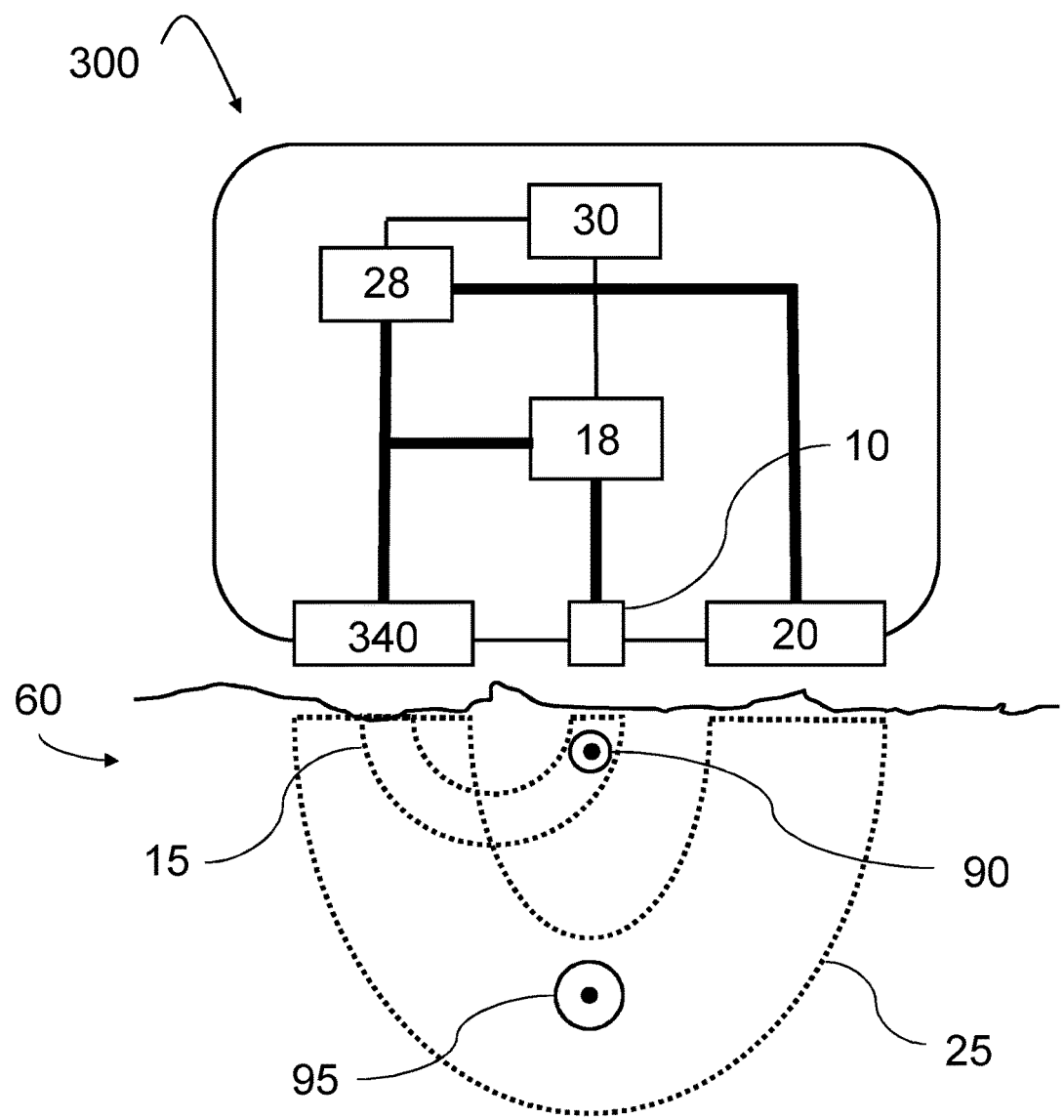
FIG. 1 diagrammatically shows a first embodiment 300 of a non-invasive treatment device according to the invention in use when treating skin.

FIG. 1 schematically shows a first embodiment of a non-invasive skin treatment device 300 comprising a first r.f. treatment electrode 10, a return electrode 340, and a second r.f. treatment electrode 20, each of which have an electrical skin contact area. The device 300 further comprises a first r.f. generator 18 configured and arranged to be operated in bipolar mode by being electrically connected to the first r.f. treatment electrode 10 and the return electrode 340.

The device 300 also comprises a second r.f. generator 28, configured and arranged to be operated in bipolar mode by being electrically connected to the second r.f. treatment electrode 20 and the return electrode 340. The return electrode 340 is configured and arranged to allow electrical current to pass through both the first inner region 15 and the second inner region 25 of the skin and an outer surface of skin. The second r.f. generator 28 is configured and arranged such that, in use for heating, an r.f. current is applied between the second r.f. treatment electrode 20 and the combined return electrode 340 through the first inner region 15.

The device may have two distinct r.f. generators, or a single r.f. generator configured to provide both the first r.f. current and the second r.f. current during, respectively, the first and second use. For example, for simultaneous application of the first r.f. current and the second r.f. current, a single transformer may be used with potential tapping having an approximately 1:2 voltage ratio (e.g. 40 V for second r.f. current and 80 V for first r.f. current). The device 300 further comprises a controller 30, electrically connected to the first r.f. generator 18 and the second r.f. generator 28, and configured and arranged to selectively activate the first 18 and second r.f. generators either simultaneously, separately or alternately.

The device 300 is configured and arranged to be brought into close proximity of human or animal skin 60, with the treatment electrodes 10, 20 and the return electrode 340 facing the outer layer of the skin. Each electrode comprises a skin contact area, which provides electrical contact with the skin 60 during use of that electrode. The treatment and return electrodes may make physical contact with the outer layer of the skin, or may be arranged at a small distance from the skin with a small gap between the electrodes and the skin. Typically, a conductive substance, such as a gel, is applied in this gap between the skin and the skin contact area to reduce any contact impedance between electrodes and the outer layer of the skin.

The treatment device 300 is configured and arranged to heat the first inner region 15 and the second inner region 25 of the skin using r.f. current the first inner region 15 is substantially smaller in volume than the second inner region 25. This is determined, inter alia, by the arrangement and configuration of the treatment electrodes 10, 20 and the return electrode 340, and the ratio of the electrical skin contact areas of the electrodes 10, 20, 340.

In this example, the electrical skin contact area of the return electrode 340 is 5 or more times larger than the electrical skin contact area of the first r.f. treatment electrode 10. This ratio is predetermined and/or controlled to preferably provide r.f. heating proximate, i.e. immediately below, the first r.f. treatment electrode 10 in the first inner region 15 at the first treatment target area 90. If the electrical skin contact area of the return electrode 340 is increased compared to the electrical skin contact area of the first r.f. electrode 10, this will result in increased proximity of the treatment target area 90 to the first r.f. treatment electrode 10.

The inner regions 15, 25 may be located, inter alia, in the epidermis or dermis of the skin. The Figures are very schematic, and in practice, the second inner region 25 may be located only slightly deeper in the skin 60 than the first inner region 15.

The first r.f. treatment electrode 10 is configured and arranged to allow electrical current from the first r.f. generator 18 to pass through an outer surface of the skin and through a first inner region 15 of skin. The second r.f. treatment electrode 20 is configured and arranged to allow electrical current from the second r.f. generator 28 to pass through an outer surface of skin and through a second inner region of skin 25. Both the first r.f. treatment and the second r.f. treatment are provided by operating the electrodes in bipolar mode.

The region which the user wishes to treat may lie on the r.f. current path through the skin, or immediately adjacent to that path. The heat generated in the skin by the r.f. current may spread to adjacent tissue regions. Treatment of multiple regions, both contiguous and non-contiguous, is also possible. The device 300 may thus be configured such that a first treatment target 90, such as the collagen immediately below a wrinkle, is located within the first inner region 15 volume, or that the first inner region 15 is proximate the first treatment target 90. Similarly, the device 300 may be configured such that a second treatment target 95, such as the collagen immediately below a wrinkle, is located within the second inner region 25 volume, or that the second inner region 25 is proximate the second treatment target 95.

When in use for heating the first inner region 15, the first r.f. generator 18 generates an r.f. current which is suitable to heat the skin 60. In other words, the heating occurs in the proximity of the first r.f. treatment electrode 10. The first r.f. treatment electrode 10 allows the r.f. current to pass through an outer surface of skin, and through the first inner region 15 of skin such that a first target area 90 is heated appropriately by the current flowing through the first inner region 15. The current also flows through a further outer surface of the skin to the return electrode 340.

The r.f. current for heating the first inner region 15 and the second inner region 25 may have an AC waveform, with a frequency in the range of 0.3-100 MHz and a power in the range of 1-400 W. A typical frequency used is 0.5-1 MHz, with a power of 25-100 W. The voltage and current for the first and second r.f. energies may differ from each other, and depends on, inter alia, the treatment being performed and the depth of the inner regions 15, 25 below the outer layer of skin.

For example, the first r.f. treatment electrode 10 may be circular in a cross-section through the electrical skin contact area. The electrical skin contact area is proximate and approximately parallel to an outer layer of skin 60 during use. If the first r.f. treatment electrode 10 has a diameter of 0.5 mm in that cross-section, and the distance in the plane of the contact areas of the electrodes 10, 340, is 1 mm, then a typical voltage of the first r.f. may be 15-60V. Treatment duration is typically less than 1 second, in a single pulse or multiple pulses.

The electrical skin contact area of the second r.f. treatment electrode 20 is significantly larger than the electrical skin contact area of the first r.f. treatment electrode 10 this ratio in electrode area is a major factor in determining the ratio between the second volume 25 and the first volume 15. In this example, the electrical skin contact area of the second r.f. treatment electrode 20 is 5 or more times larger than the electrical skin contact area of the first r.f. treatment electrode 10. However, the electrical skin contact area of the second r.f. treatment electrode 20 may be equal to, or significantly smaller than, the electrical skin contact area of the return electrode 340.

The smallest dimension of the electrical skin contact area of the second r.f. treatment electrode 20 is preferably more than 1 mm. The second r.f. treatment will typically take place at a voltage of 50-100V, and the second treatment duration will typically be more than 1 second, using a sustained single pulse, or multiple pulses over a sustained time.

The path of the r.f. current through the first 15 and second 25 inner regions of the skin 60 is determined, inter alia, by the position, geometry and size of the treatment electrodes 10, 20, and the position of electrical contact on the outer layer of the skin. Smaller influences on the path taken may be due to, inter alia, the impedance of the different tissue types through which the r.f. current flows. By providing both the second 20 r.f. treatment electrode and the first r.f. treatment electrode 10 in the same device, the positional relationship between the second inner region 25 and the first inner region 15 may be fixed, or at least made more predictable compared to the separate probes found in the prior art.

Typically, the first r.f. treatment electrode 10, having its largest dimension in a cross-section, comprised in the electrical skin contact area, of 0.1-1 mm, is used for ablative or non-ablative skin rejuvenation. The electrical skin contact area of the second r.f. treatment electrode 20 will be substantially larger. In this example, the corresponding second r.f. treatment electrode 20 may have its largest dimension, comprised in the electrical skin contact area, of 5 mm-10 mm for skin tightening.

The first r.f. treatment electrode 10 may be circular, annular, oval or rectangular in a cross-section comprised in the electrical skin contact area. The geometry of the second r.f. treatment electrode 20 in a cross-section comprised in the electrical skin contact area depends on, inter alia, the preferred mode of movement during use, (for example, whether the device 300 will be stamped in steps onto an outer layer of the skin 60, or continuously glided), the area of skin to be treated, the desired heating volume for the second heating, as well as the desired balance between first and second inner regions of skin tissue. These factors may also depend on the site on the body, and first/second treatment targets 90, 95 being treated.

Figure 3A:
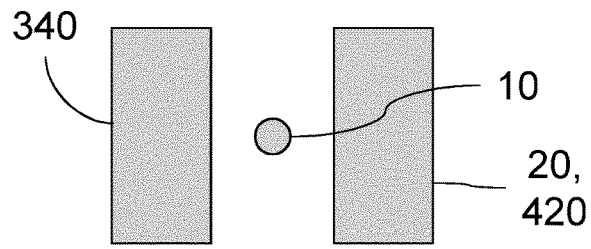
FIGS. 3A-3D depict four examples of electrode geometries and configurations comprising a single first r.f. treatment electrode.

An example of the electrode geometry as viewed in a cross-section through the contact plane, for the device 300 of FIG. 1, is depicted in FIG. 3A. The first r.f. treatment electrode 10 is round in cross-section and is located between a rectangular second r.f. treatment electrode 20 and a rectangular first return electrode 340, when considered in a plane comprising the electrical skin contact areas of all three electrodes. For example, if, in the plane comprising the skin electrical contact area, the return electrode 340 is located about 10 mm from the centroid of the cross-section of the second r.f. treatment electrode 20, then the voltage range for the second r.f. treatment electrode, when operating to promote tightening in the skin, may be in the range of 50-100V for a duration of more than 1 second.

Figure 4A:
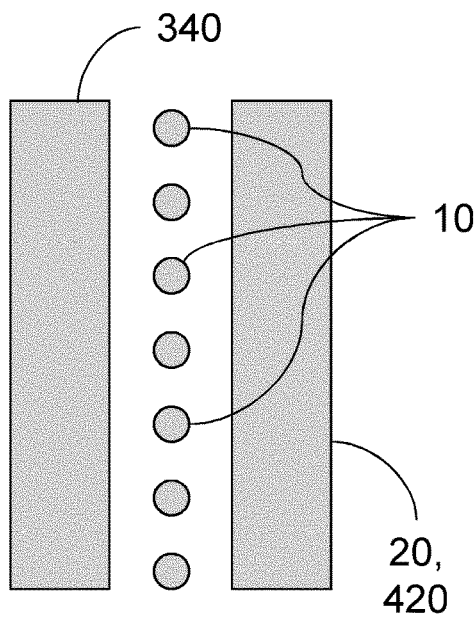
FIGS. 4A-4D depict four examples of electrode geometries and configurations comprising a plurality of first r.f. treatment electrodes and two further electrodes.

An array of a plurality of first r.f. treatment electrodes 10 may also be provided for use in a fractional treatment. An example of this electrode geometry, as viewed in a cross-section through the skin contact area, for the device 300 of FIG. 1, is depicted in FIG. 4A. A plurality of first r.f. treatment electrodes 10, round in cross-section, are arranged in a row in a plane comprising the electrical skin contact areas, and are approximately equidistantly arranged between an extended rectangular second r.f. treatment electrode 20 and an extended rectangular first return electrode 340.

Figure 4B:
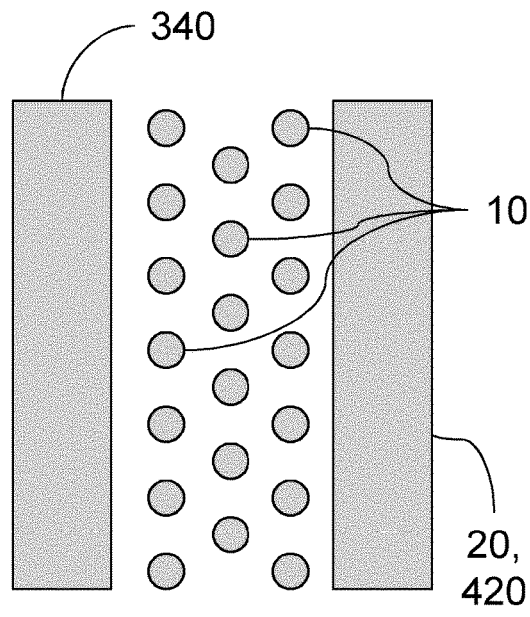

FIG. 4B also depicts a plurality of first r.f. treatment electrodes 10, round in cross-section, between an extended rectangular second r.f. treatment electrode 20 and an extended rectangular first return electrode 340. In this example, the r.f. treatment electrodes 10 are arranged in three rows in a plane comprising the electrical skin contact areas, the central row being offset by half the pitch of the first r.f. treatment electrodes 10 in the direction of extension of the rows.

Figure 4C:
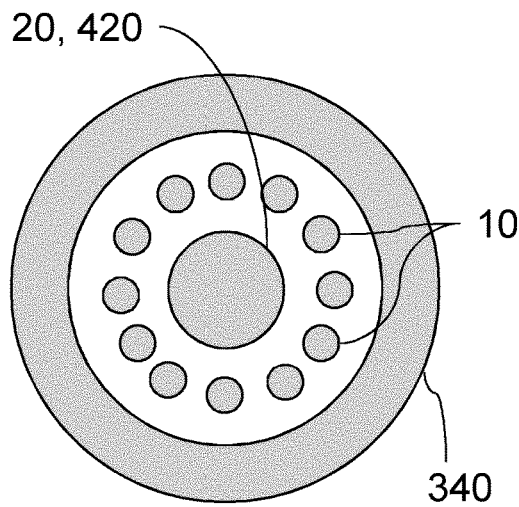

FIG. 4C depicts a plurality of first r.f. treatment electrodes 10, round in cross-section, arranged in a single circular path, approximately equidistantly arranged between a circular second r.f. treatment electrode 20 and an annular first return electrode 340, the first return electrode 340 surrounding both the second r.f. treatment electrode 20 and the first r.f. treatment electrodes 10 in a plane comprising the skin contact area.

Figure 4D:
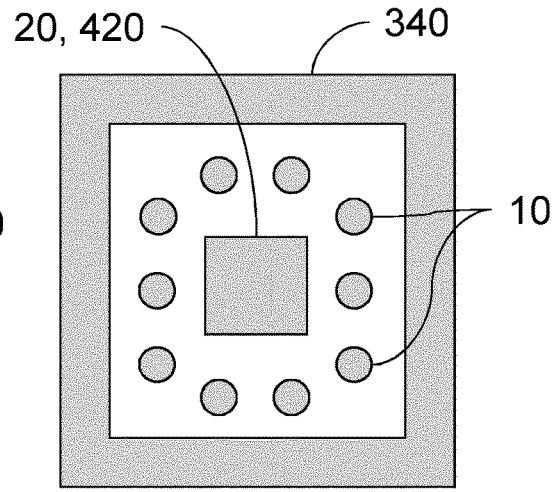

FIG. 4D depicts a plurality of first r.f. treatment electrodes 10, round in cross-section, arranged in a single rectangular path, approximately equidistantly arranged between a square second r.f. treatment electrode 20 and a square-frame first return electrode 340, the first return electrode 340 surrounding both the r.f. treatment electrode 20 and the first r.f. treatment electrodes 10 in a plane comprising the skin contact area.

In use, the treatment device 300 may be configured and arranged to influence the degree of coincidence of the first inner region 15 and the second inner region 25 by, inter alia, arranging the second r.f. treatment electrode 20 closer to the first r.f. treatment electrode 10, by changing the cross-sectional geometry of the electrodes 10, 20, 340, by changing the distance between the return electrode 340 and the first r.f. treatment electrode 10, and/or by careful selection of the r.f. energy parameters.

The treatment device 300 may be operated in a first r.f. heating mode, a second r.f. heating mode and a simultaneous treatment mode using a first and a second r.f. heating current. The r.f. generators may be controlled by the controller 30 to provide consistent energy dosages, or variable energy dosages as part of a treatment regime. A combination of sequential or alternating treatments is possible. This may provide gradual tissue contraction. Also pulsing sequences may be optimized to minimize pain or discomfort experienced by the user.

For example, the device 300 may be configured such that the first inner region 15 is completely comprised in the second inner region 25. The first step in the regime may be a suitably long application of second r.f. current to tighten the skin lasting several seconds, followed by a delay of 300 milliseconds or less to allow some thermal dissipation in the second inner skin region, followed by a brief pulse of less than 1 second of first r.f. current to provide skin rejuvenation.

The delay time between the second treatment and the first treatment should not exceed the thermal relaxation time of the dermis (100 ms) and can even be approximately zero. A short delay time allows heated tissue to be treated by the first r.f. current, which may advantageously provide deeper and wider lesions, with a lower first r.f. voltage compared to a conventional device where only a first r.f. current is applied.

The order may be reversed, so that the first r.f. heating occurs first, followed by the second r.f. heating; the first inner region 15 of heated tissue is further heated by the second r.f. current, and may influence the path of the second r.f. current during the second heating.

Figure 3B:
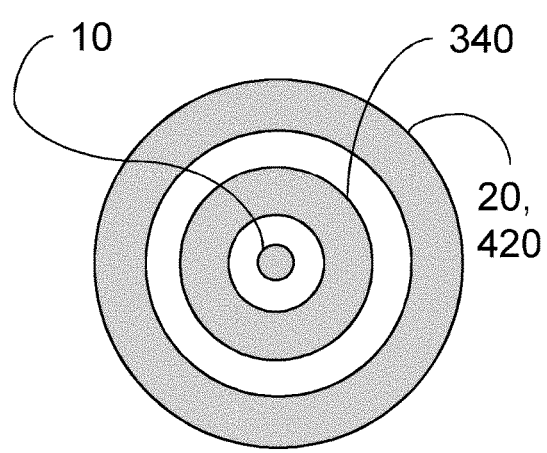
Figure 3C:
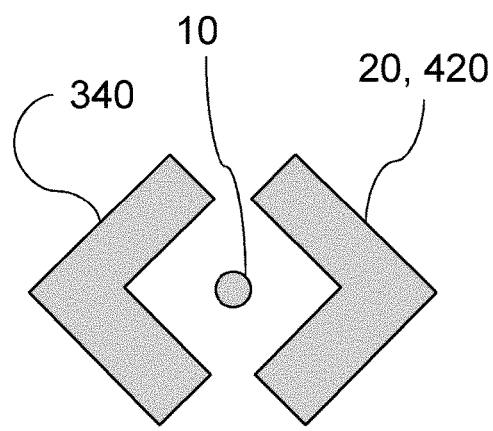
Figure 3D:
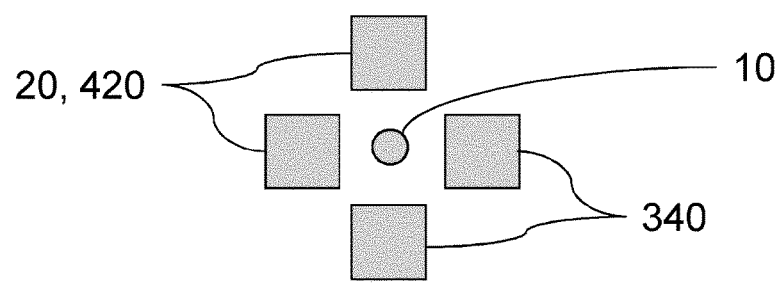

Further examples of the electrode geometry as viewed in a cross-section through the electrical skin contact areas of the electrodes are depicted in FIGS. 3B to 3D. Typically, the spacing, in a plane comprising the electrical skin contact area, between the edge of the first r.f. treatment electrode 10 and the edge of the return electrode 340 will be in the range of 500 micron to 1 mm.

In FIG. 3B, the first r.f. treatment electrode 10, round in cross-section, is located at the centre of an annular return electrode 340. In FIG. 3C, the first r.f. treatment electrode 10, round in cross-section, is located proximate a "v-shaped" return electrode 340 along the axis of symmetry of the return electrode 340, and is partially surrounded by said return electrode 340.

Although single electrodes are depicted and described, for some of the embodiments, a plurality of electrodes or arrays of electrodes, either for the first/second treatment and/or the first/second return electrode may alternatively be applied. Such a plurality of electrodes may be operated individually, in groups or all together to provide a high degree of control over the paths of the r.f. current through the skin 60. For example, in FIG. 3D, the first r.f. treatment electrode 10, round in cross-section, is located approximately equidistantly between four return electrodes 340, which are square in cross-section. The four square return electrodes 340 may be electrically interconnected and operated using the same second r.f. energy parameters, or they may each receive individual second r.f. energy parameters. They may also be operated as a group or individually when functioning as the return electrode 340 such flexibility allows a high degree of control over the path of the first r.f. current through the first inner region 15 of skin 60.

Figure 2:
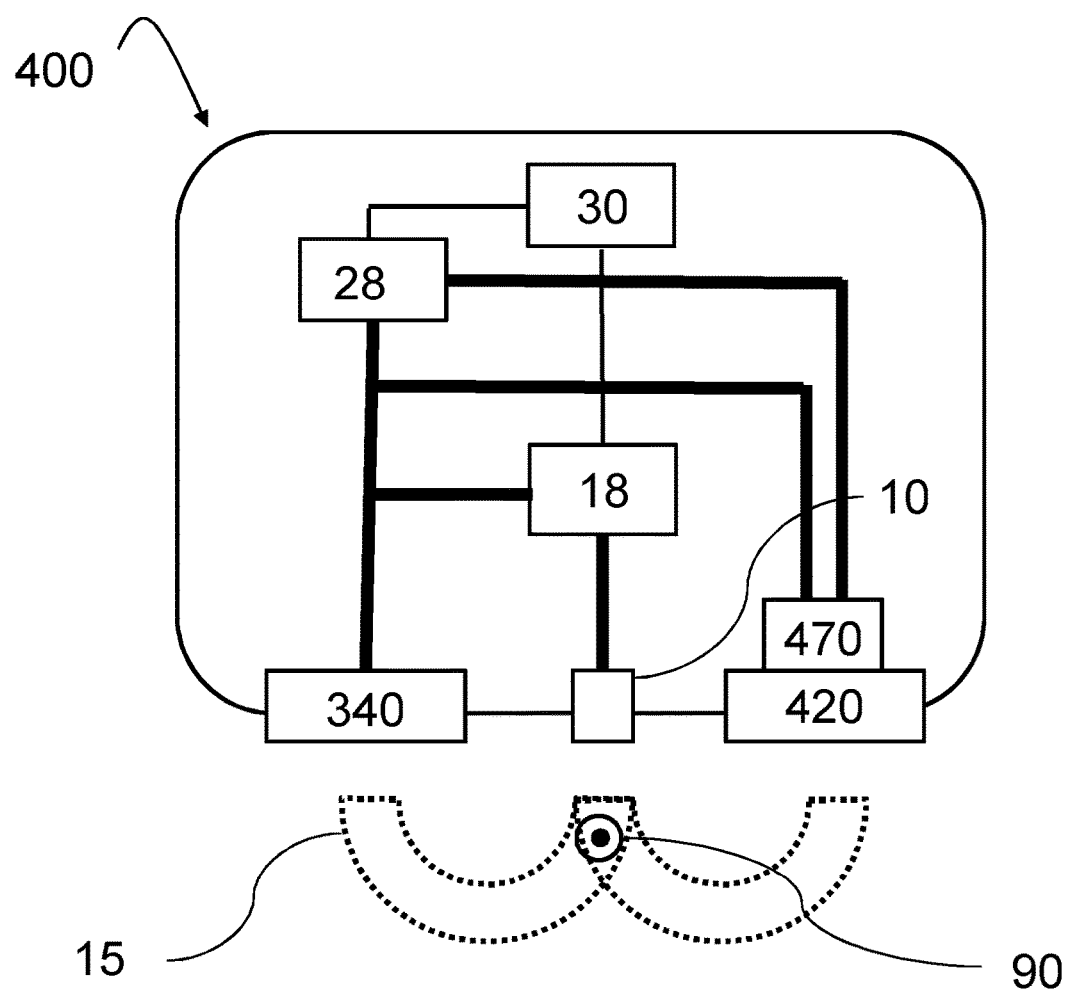
FIG. 2 shows a second embodiment 400 of the non-invasive treatment device according to the invention in use when providing a first r.f. electrical current to a first inner region of the skin.

FIG. 2 depicts a second embodiment 400 of the treatment device, having the following differences compared to FIG. 1:

the second r.f. treatment electrode 20 has been replaced by a further return electrode 420;

the treatment device 400 further comprises an electrode function controller 470, electrically connected to the combined electrode 420 and to both the first r.f. generator 18 and the second r.f. generator 28 such that the functions may be switched between them;

the further return electrode 420 is configured to operate separately as either a second r.f. treatment electrode, providing bipolar treatment in combination with the return electrode 340, or a return electrode providing bipolar treatment in combination with the first r.f. treatment electrode 10.

Note that, for clarity, the second inner skin region 25 and the skin 60 are not depicted. However, these aspects will be similar to those depicted in FIG. 1.

In other words, during heating of the first inner region 15, the bipolar treatment is provided by the first r.f. treatment electrode 10 and two return electrodes—the return electrode 340 and the further return electrode 420. The first r.f. generator 18 is configured and arranged such that an r.f. current is applied between the first r.f. treatment electrode 10 and both the return electrode 340 and the further return electrode 420 through the first inner region 15.

During heating of the second inner region 25, the bipolar treatment is provided by the second r.f. treatment electrode 420 and the return electrode 340. The second r.f. generator 28 is configured and arranged such that an r.f. current is applied between the second r.f. treatment electrode 420 and the return electrode 340 through the second inner region 25. The electrode function controller 470 is configured and arranged to select the function performed by the further return electrode 420 either as a return electrode or as a second r.f. treatment electrode. In this embodiment, it is not possible to perform both treatments simultaneously. However, alternate and sequential treatments are still possible.

This embodiment 400 increases the area of the first return electrode 340 during the first heating, so that there is a reduced chance of excessive heating below the first return electrode 340, and the heating is concentrated proximate the first r.f. treatment electrode 10.

The further return electrode 420 may be implemented as the same conducting body electrically connected to both the first r.f. generator 18 and the second r.f. generator 28 via the electrode function controller 470. Alternatively, the further return electrode 420 may comprise a second r.f. treatment electrode and a return electrode that are physically distinct, but electrically coupled.

When compared to the treatment device of FIG. 1, the device 400 of FIG. 2 may provide a higher degree of coincidence between the first inner region 15 and the second inner region 25. For some treatments, the device 400 may be configured and arranged such as to cause the first inner region 15 to be completely comprised in the second inner region 25.

As shown in FIG. 1, the electrode geometry in a cross-section of the electrical skin contact area may be as depicted in FIG. 3A. The first r.f. treatment electrode 10 is round in cross-section and located, in a plane comprising the electrical skin contact areas of the electrodes, between the rectangular further return electrode 420 and the rectangular return electrode 340.

A further example of the electrode geometry for the device 400 is depicted in FIG. 4A. A plurality of first r.f. treatment electrodes 10, round in cross-section, are arranged in a row in a plane comprising the skin contact areas, approximately equidistantly arranged between a further return electrode 420 and the return electrode 340.

FIG. 4B also depicts a plurality of first r.f. treatment electrodes 10, round in cross-section, arranged between a further return electrode 420 and the return electrode 340. In this example, the r.f. treatment electrodes are arranged in three rows in a plane comprising the skin contact area, the central row being offset by half the pitch of the first r.f. treatment electrodes 10 in the direction of extension of the rows.

FIG. 4C depicts a plurality of first r.f. treatment electrodes 10, round in cross-section, arranged in a single circular path, approximately equidistantly between a circular further return electrode 420, and an annular return electrode 340, the annular return electrode 340 surrounding, in a plane comprising the electrical skin contact areas, both the further return electrode 420 and the first r.f. treatment electrodes 10.

FIG. 4D depicts a plurality of first r.f. treatment electrodes 10, round in cross-section, arranged in a single rectangular path, approximately equidistantly between a square further return electrode 420 and a square-frame return electrode 340, the return electrode 340 surrounding, in a plane comprising the electrical skin contact areas, both the further return electrode 420 and the first r.f. treatment electrodes 10.

It may be advantageous if the treatment device further comprises an impedance measurement circuit, connected to one of the electrodes, and configured and arranged to measure, in use, the impedance of the radio-frequency current path through the inner region of skin. A lower impedance would increase the electrical transmission of the radio-frequency current through the skin. If the impedance measurement circuit is connected to the r.f. generator, it may be configured and arranged to select at least one parameter of the r.f. treatment current in accordance with the impedance measured. Suitable parameters may be: the duration that the current is applied, the voltage, the frequency, pulse duration and duty cycle, and the maximum current to be applied.

Similarly, skin contact can be detected by using an appropriate sensor, for example a capacitance sensor, or by measuring the skin impedance with a small measuring (pre)pulse of about 20V.

It should be noted that the above-mentioned embodiments illustrate rather than limit the invention, and that those skilled in the art will be able to design many alternative embodiments.

In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer.

The word "module" should not be interpreted to mean that the functionality and hardware are distinguishable in the device. It is used to indicate a functionality that the device comprises, and, in practice, different "modules" may use partly the same or entirely the same hardware and optical components.

In the device claim enumerating several means, several of these means may be embodied by one and the same item of hardware. The mere fact that certain measures are recited in mutually different dependent claims does not indicate that a combination of these measures cannot be used to advantage.

OVERVIEW OF REFERENCE NUMBERS 10 first r.f. treatment electrode
15 first inner region of the skin where r.f. treatment current may flow
18 first r.f. generator
20 second r.f. treatment electrode
25 second inner region of the skin where r.f. treatment current may flow
28 second r.f. generator
30 controller
60 Skin
90 first treatment target (in first inner region of the skin)
95 second treatment target (in second inner region of the skin)
300 Bipolar skin treatment device ($1^{st}$ embodiment)
340 return electrode
400 Bipolar skin treatment device ($2^{nd}$ embodiment)
420 further return electrode—first return and second treatment
470 electrode function controller

The invention claimed is:

1. A non-invasive treatment device for heating a first inner region and a second inner region of skin using radio-frequency (r.f.) electrical current, the second inner region being at a deeper location in the skin than the first inner region, the device comprising:
a first r.f. treatment electrode configured and arranged to allow r.f. electrical current to pass through an outer surface of the skin and through the first inner region;
a return electrode configured and arranged to allow r.f. electrical current to pass through the first inner region and the outer surface of the skin, wherein the return electrode is used in combination with the first r.f. treatment electrode for a skin rejuvenation treatment;
a first r.f. generator configured and arranged such that, in use for heating the first inner region, a first r.f. current is applied through the first inner region between the first r.f. treatment electrode and the return electrode operating in bipolar mode;
a second r.f. treatment electrode configured and arranged to allow r.f. electrical current to pass through the outer surface of the skin and through the second inner region;
the return electrode being further configured and arranged to allow r.f. electrical current to pass through the second inner region and the outer surface of the skin, wherein the return electrode is used in combination with the second r.f. treatment electrode for a skin tightening treatment; and
a second r.f. generator configured and arranged such that, in use for heating the second inner region, a second r.f. current is applied through the second inner region between the second r.f. treatment electrode and the return electrode operating in bipolar mode;
wherein a smallest distance between the first r.f. treatment electrode and the return electrode is less than a smallest distance between the second r.f. treatment electrode and the return electrode;

wherein the first r.f. treatment electrode, the second r.f. treatment electrode and the return electrode each comprise an electrical skin contact area, a maximum dimension of the first r.f. treatment electrode proximate the electrical skin contact area of the first r.f. treatment electrode being less than or equal to 1 mm, and the electrical skin contact area of the return electrode being 5 or more times larger than the electrical skin contact area of the first r.f. treatment electrode, wherein, for skin rejuvenation, a skin region effectively heated by the first r.f. electrical current will be at a first treatment target proximate to, immediately below, the first r.f. treatment electrode while reducing a possibility of undesirable hotspots proximate to the return electrode, wherein the electrical skin contact area of the second r.f. treatment electrode is 5 or more times larger than the electrical skin contact area of the first r.f. treatment electrode, wherein, for skin tightening, a skin region effectively heated by the second r.f. electrical current will be at a second treatment target intermediate the second r.f. treatment electrode and the return electrode; the device further comprising:

a controller to selectively activate the first r.f. generator and the second r.f. generator either separately or alternately for applying both skin rejuvenation and skin tightening treatments at a same position of the treatment device on the skin.

2. The treatment device according to claim 1, wherein, when the treatment device is in operation for heating the first inner region, the second r.f. treatment electrode is configured and arranged as a further return electrode to allow r.f. electrical current to pass through the first inner region and the outer surface of the skin, and wherein the first r.f. generator is configured and arranged such that an r.f. electrical current is applied between the first r.f. treatment electrode and both the return electrode and the further return electrode through the first inner region, and wherein a total of the electrical skin contact areas of the return electrode and the further return electrode is 5 or more times larger than the electrical skin contact area of the first r.f. treatment electrode.

3. The treatment device according to claim 1, wherein the device comprises a plurality of first r.f. treatment electrodes, the plurality of first r.f. treatment electrodes and the return electrode being configured and arranged to allow r.f. electrical current to pass through the outer surface of the skin and through a plurality of first inner regions, and wherein the first r.f. generator is configured and arranged to apply r.f. electrical current to each of the plurality of first r.f. treatment electrodes and to each of the plurality of first inner regions either alternately or simultaneously.

4. The treatment device according to claim 1, wherein the device comprises a plurality of second r.f. treatment electrodes, the plurality of second r.f. treatment electrodes and the return electrode being configured and arranged to allow r.f. electrical current to pass through the outer surface of the skin and through a plurality of second inner regions, and wherein the second r.f. generator is configured and arranged to apply r.f. electrical current to each of the plurality of second r.f. treatment electrodes and to each of the plurality of second inner regions either alternately or simultaneously.

* * * * *